US010842654B2

(12) United States Patent
Kim et al.

(10) Patent No.: US 10,842,654 B2
(45) Date of Patent: Nov. 24, 2020

(54) STENT WITH SEGMENTS CAPABLE OF UNCOUPLING DURING EXPANSION

(71) Applicant: COOK MEDICAL TECHNOLOGIES LLC, Bloomington, IN (US)

(72) Inventors: Woong Kim, West Lafayette, IN (US); Keith R. Milner, West Lafayette, IN (US); Richard A. Swift, South Bend, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 16/033,453

(22) Filed: Jul. 12, 2018

(65) Prior Publication Data
US 2019/0021885 A1    Jan. 24, 2019

Related U.S. Application Data

(60) Provisional application No. 62/534,306, filed on Jul. 19, 2017.

(51) Int. Cl.
| *A61F 2/915* | (2013.01) |
| *A61F 2/82* | (2013.01) |
| *A61F 2/958* | (2013.01) |

(52) U.S. Cl.
CPC .............. *A61F 2/82* (2013.01); *A61F 2/915* (2013.01); *A61F 2/958* (2013.01);
(Continued)

(58) Field of Classification Search
CPC .. A61F 2002/91591; A61F 2002/91583; A61F 2/89; A61F 2/82;
(Continued)

(56) References Cited

U.S. PATENT DOCUMENTS 5,741,327 A * 4/1998 Frantzen ................... A61F 2/91
                                                    606/153
5,797,951 A * 8/1998 Mueller .................... A61F 2/93
                                                    606/191
(Continued)

FOREIGN PATENT DOCUMENTS

| DE | 199 50 756 | 8/2000 |
| WO | 2006/116383 | 11/2006 |

OTHER PUBLICATIONS

Search Report for EP18275098.4 dated Dec. 3, 2018, 8 pgs.
European Search Report in related European Application No. 18275098. 4, dated Jul. 8, 2020 (6 pages).

*Primary Examiner* — Alvin J Stewart
(74) *Attorney, Agent, or Firm* — Brinks Gilson & Lione

(57) ABSTRACT

Examples of a stent are provided with interlocking joints removably coupling adjacent axial stent segments. Mating elements forming the interlocking joints maintain engagement when the stent is in the radially compressed configuration, for example, during tracking of the stent to a treatment site of a body vessel, and become disengaged during radial expansion of the stent. When disengaged, the disconnected the axial stent segments remain discrete stent structures separated from one another along the point of treatment.

20 Claims, 5 Drawing Sheets

FIG. 2

(52) U.S. Cl.
CPC ... *A61F 2002/826* (2013.01); *A61F 2002/828* (2013.01); *A61F 2002/91541* (2013.01); *A61F 2002/91558* (2013.01); *A61F 2002/91566* (2013.01); *A61F 2002/91591* (2013.01); *A61F 2220/0033* (2013.01)

(58) Field of Classification Search
CPC .. A61F 2002/91575; A61F 2002/91566; A61F 2002/91558; A61F 2002/9155; A61F 2002/91541; A61F 2002/91533
See application file for complete search history.

(56) References Cited

U.S. PATENT DOCUMENTS

| | | | |
|---|---|---|---|
| 6,251,134 B1* | 6/2001 | Alt | A61F 2/90 606/194 |
| 7,789,906 B2* | 9/2010 | Blank | A61F 2/91 623/1.16 |
| 8,603,154 B2* | 12/2013 | Strauss | A61F 2/915 623/1.16 |
| 8,961,585 B2* | 2/2015 | Ma | A61F 2/91 623/1.15 |
| 9,943,426 B2* | 4/2018 | Sirhan | A61F 2/89 |
| 10,231,856 B2* | 3/2019 | Milner | A61F 2/844 |
| 10,271,976 B2* | 4/2019 | Sirhan | A61F 2/89 |
| 2002/0111671 A1* | 8/2002 | Stenzel | A61F 2/91 623/1.16 |
| 2004/0236406 A1* | 11/2004 | Gregorich | A61F 2/91 623/1.16 |
| 2005/0055080 A1 | 3/2005 | Stephanous | |
| 2006/0020324 A1* | 1/2006 | Schmid | A61F 2/856 623/1.16 |
| 2006/0030932 A1* | 2/2006 | Kantor | A61F 2/91 623/1.16 |
| 2006/0069424 A1* | 3/2006 | Acosta | A61F 2/91 623/1.12 |
| 2006/0195175 A1* | 8/2006 | Bregulla | A61F 2/91 623/1.15 |
| 2007/0100431 A1* | 5/2007 | Bonsignore | A61F 2/915 623/1.15 |
| 2007/0213810 A1* | 9/2007 | Newhauser | A61F 2/91 623/1.16 |
| 2007/0219612 A1* | 9/2007 | Andreas | A61B 17/12022 623/1.11 |
| 2007/0219613 A1* | 9/2007 | Kao | A61B 17/12022 623/1.11 |
| 2007/0233232 A1* | 10/2007 | St. Germain | A61F 2/91 623/1.15 |
| 2008/0234795 A1* | 9/2008 | Snow | A61F 2/91 623/1.11 |
| 2009/0005848 A1* | 1/2009 | Strauss | A61F 2/91 623/1.2 |
| 2009/0036970 A1* | 2/2009 | Ma | A61F 2/91 623/1.15 |
| 2009/0234429 A1* | 9/2009 | Lau | A61F 2/91 623/1.12 |
| 2011/0130822 A1* | 6/2011 | Cottone | A61F 2/91 623/1.15 |
| 2011/0152997 A1* | 6/2011 | Kelly | A61F 2/958 623/1.12 |
| 2011/0190861 A1* | 8/2011 | Pericevic | A61F 2/91 623/1.11 |
| 2013/0178926 A1* | 7/2013 | Denison | A61F 2/88 623/1.16 |
| 2014/0364935 A1* | 12/2014 | Eli | A61F 2/91 623/1.12 |
| 2016/0038318 A1* | 2/2016 | Weier | A61F 2/93 623/1.16 |
| 2016/0206450 A1* | 7/2016 | Mitsudo | A61L 31/022 |
| 2017/0290686 A1* | 10/2017 | Sirhan | A61F 2/89 |
| 2019/0021885 A1* | 1/2019 | Kim | A61F 2/82 |

* cited by examiner

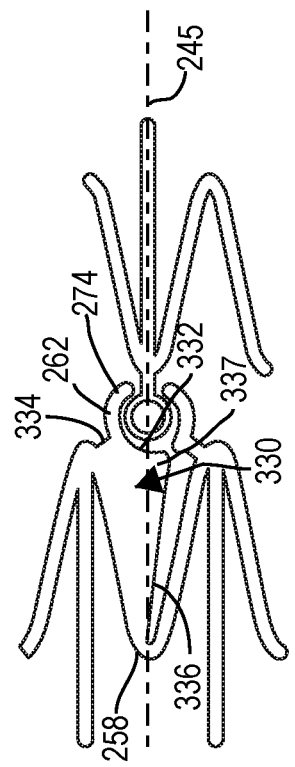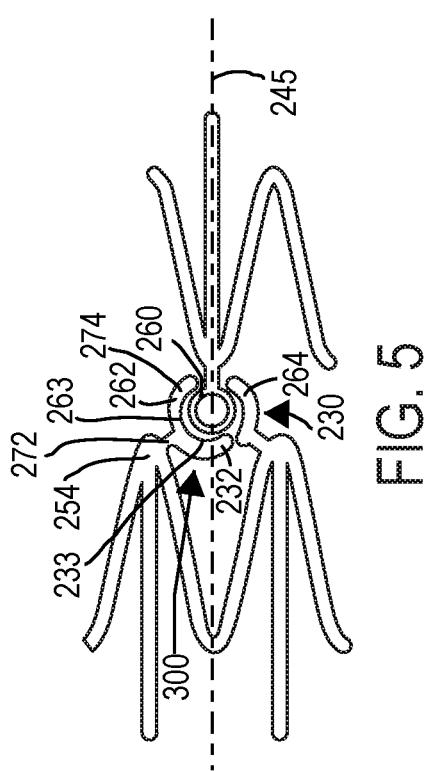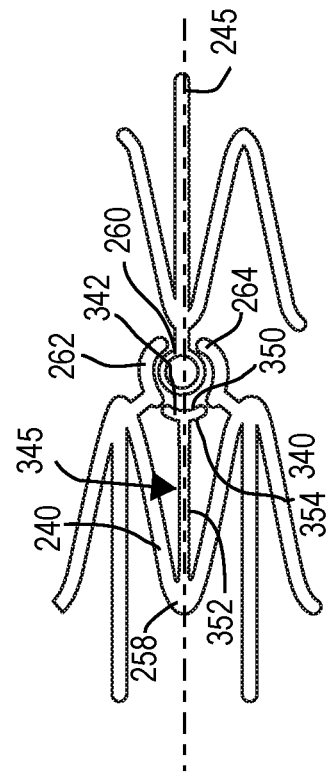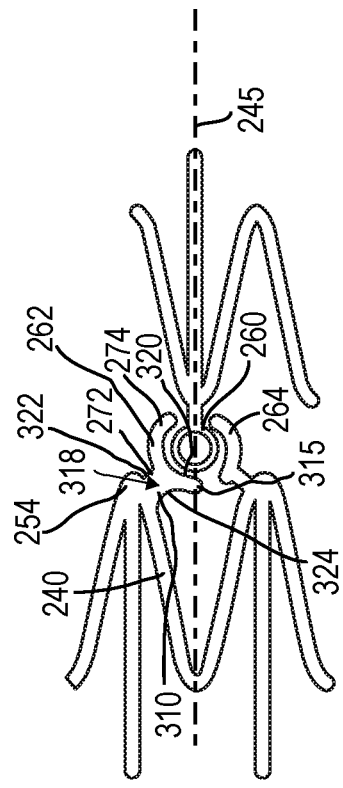
FIG. 5
FIG. 7
FIG. 6
FIG. 8

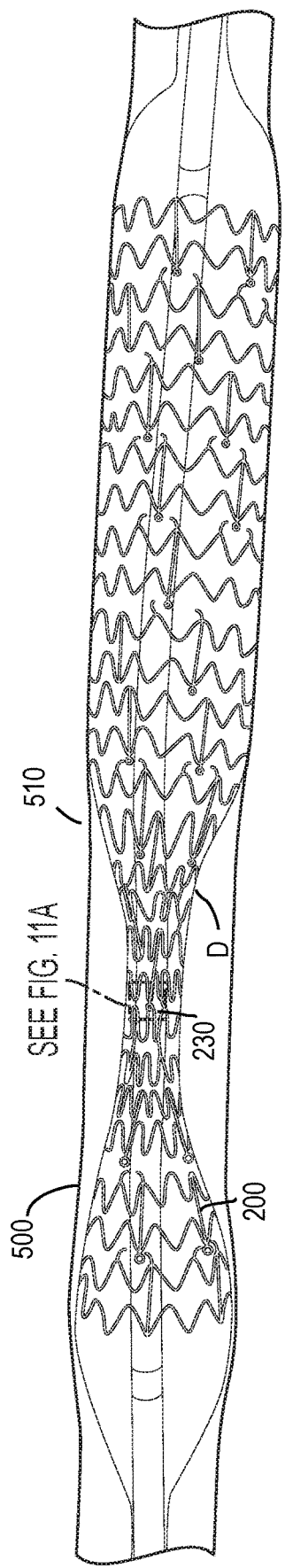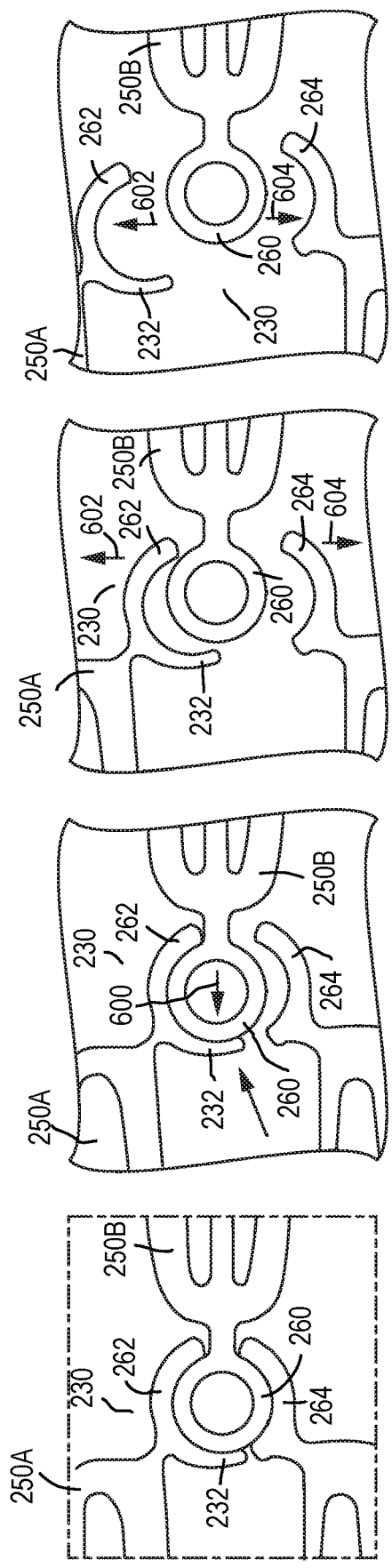

STENT WITH SEGMENTS CAPABLE OF UNCOUPLING DURING EXPANSION

PRIORITY CLAIM

This invention claims the benefit of priority of U.S. Provisional Application Ser. No. 62/534,306, entitled "Stent with Segments Capable of Uncoupling During Expansion," filed Jul. 19, 2017, the disclosure of which is hereby incorporated by reference in its entirety.

BACKGROUND

The present disclosure relates generally to medical devices, and particularly, to intraluminal support frames or stents for implantation within a human or animal body for repair of damaged vessels, ducts, or other physiological pathways.

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened be a variety of conditions, such as aneurysms.

Intraluminal support frames, sometimes referred to as stents, provide an artificial mechanism to support a body vessel. Stents are typically tubular-shaped members that are placed in the lumen of the vessel and, once deployed, exert a radially-outward directed force onto the vessel wall to provide the desired support.

Stents are typically positioned at the point of treatment or target site by navigation through the vessel, and possibly other connected vessels, until the point of treatment is reached. This navigation may require the stent to be able to move axially through the vessel(s) prior to deployment, while still maintaining the ability to exert an outward force on the interior wall once deployed. Accordingly, stents typically have radially unexpanded and expanded configurations. In the unexpanded configuration, the stent has a relatively small diameter that allows it to move axially through the vessel. In the expanded configuration, the stent has a relatively large diameter that allows it to exert an outward force on the interior wall of the lumen, thereby providing the desired support to the vessel.

Stents are typically either self-expanding stents or balloon expandable stents, which categorizes how the stents move from the radially unexpanded configuration to the expanded configuration. Balloon expandable stents typically provide greater radial force and circumferential compression resistance over self-expanding stents. However, balloon expandable stents generally are stiffer structures. Their inflexibility and lack of elasticity limit their longitudinal flexibility and ability to conform to tortuous vessels, such as the superficial femoral artery (SFA), and can lead to permanent deformation when subjected to high levels of motion. For example, certain vessels, such as the SFA, provide a high-level motion environment that contributes to greater bending and longitudinal compression loads to stent structures than vessels positioned in less motion environments. Thus, the use of self-expanding stents in this environment is typically more attractive as balloon expandable stents may be prone to experience permanent deformation in such environment, unless the stent architecture of balloon expandable stents can be improved for such environment.

SUMMARY

In one example, a stent is disposed about a longitudinal axis, and the stent has a radially compressed configuration and a radially expanded configuration. The stent includes a first stent segment and a second stent segment disposed about the longitudinal axis and axially adjacent to the first stent segment. The first stent segment includes a plurality of stent struts forming a plurality of first outer apices that extend in a first longitudinal direction. The second stent segment includes a plurality of stent struts forming a plurality of second outer apices that extend in a second longitudinal direction, opposite the first longitudinal direction. A plurality of interlocking joints removably couple the first stent segment and the second stent segment together. Each of the interlocking joints includes a first mating element, a second mating element, and a third mating element. The first mating element extends away from one of the first outer apices. The second mating element and the third mating element extend away from adjacent outer apices of the second outer apices. An axial restrictor member extends away from the second stent segment. In the radially compressed configuration, the second and third mating elements are circumferentially engageable with the first mating element, and the axial restrictor member is axially engageable with the first mating element.

In another example, the stent is disposed about a longitudinal axis, and includes a radially compressed configuration and a radially expanded configuration. The stent includes a first stent segment disposed about the longitudinal axis. The first stent segment includes a plurality of first outer apices extending in a first longitudinal direction, and a first rounded mating head extending in the first longitudinal direction from at least one of the first outer apices. The stent includes a second stent segment disposed about the longitudinal axis and axially adjacent to the first stent segment. The second stent segment includes a plurality of second outer apices extending in a second longitudinal direction. The second stent segment includes a first concave mating arm and a second concave mating arm extending in the second longitudinal direction from adjacent outer apices of the second outer apices. An axial restrictor member extends from the second stent segment. In the radially compressed configuration, the first concave mating arm and the second concave mating arm are engageable along different circumferential sides of the first rounded mating head.

In another example, a stent is disposed about a longitudinal axis. The stent includes a radially compressed configuration and a radially expanded configuration. The stent includes a first stent segment and a second stent segment adjacent thereto and disposed about the longitudinal axis. The first stent segment includes a plurality of first outer apices that extend in a first longitudinal direction. At least one of the first outer apices includes a first mating element. The second stent segment includes a plurality of second outer apices that extend in a second, opposite longitudinal direction. A pair of adjacent second outer apices includes a second mating element and a third mating element, respectively. The second stent segment includes an axial restrictor member having an engaging axial surface contactable with the first mating element during radial expansion. In the radially compressed configuration, the first mating element is circumferentially captured between the second and third mating elements.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 5-8 depict alternative configurations of the axial restrictor member associated with the interlocking joints.

FIG. 10 depicts an example of a stent in a radially expanded configuration implanted within a body vessel.

FIGS. 11A-D depict sequential order of the unlocking of the interlocking joint from the stent in the radially compressed configuration and the stent in the radially expanded configuration.

DETAILED DESCRIPTION OF THE PREFERRED EMBODIMENTS

Figure 1:
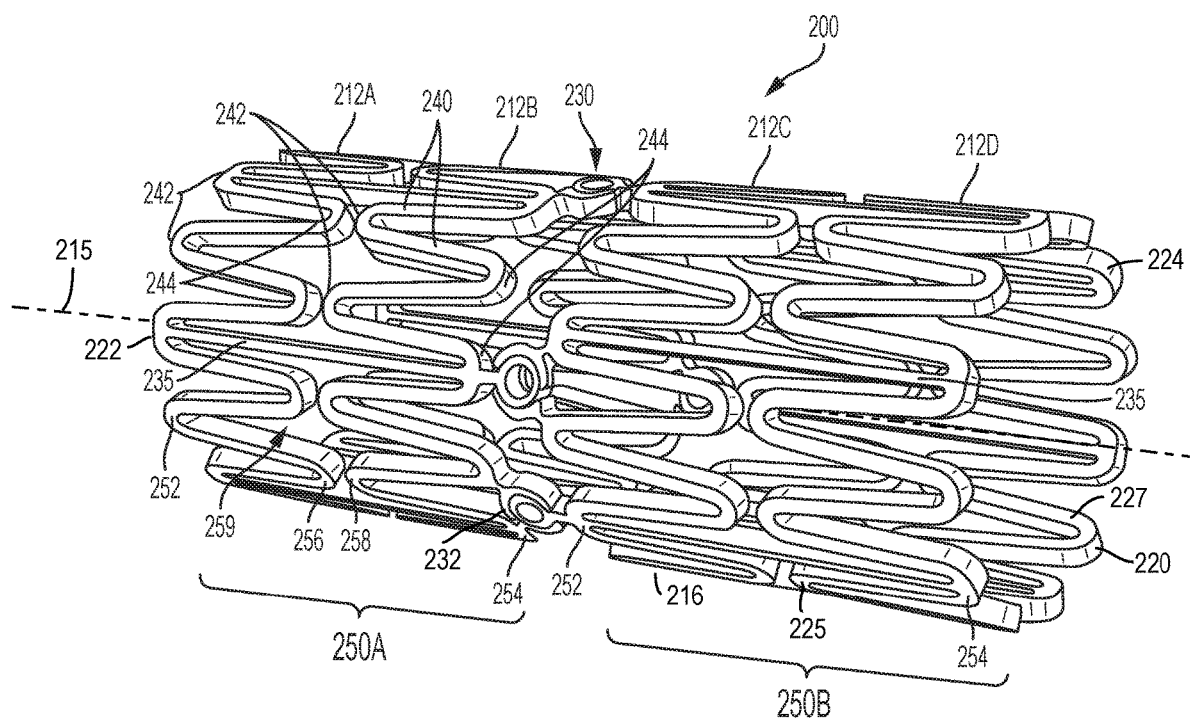
FIG. 1 is a perspective view of an example of a stent in a radially compressed configuration.

Stents for implantation within a human or animal body for repair of damaged vessels, ducts, or other physiological pathways are provided. The stent architecture may allow for segments of the stent to remain coupled for structural stability during delivery to a target site and to uncouple during radial expansion whereby the segments are at least one of longitudinally or circumferentially movable relative to one another after disengagement. Particularly, mating elements forming the interlocking joints described herein that couple adjacent segments have shown improved performance while in an interlocking relationship and further configured to disengage during expansion. For example, stents with these interlocking joints have provided suitable resistance to various mechanical loading from the vessels, such as axial loads (such as compression and tensile, especially resistance to longitudinal stretching), bending loads (such as longitudinal bending), and torque loads. Torque loading and axial loading may occur especially during maneuvering and orienting the stent to the target site. Torque loading and axial loading may also occur during balloon inflation due to uneven expansion of the balloon, thereby causing a phenomenon known as "dog-boning." Axial restrictor members may be provided to withstand overlapping or nesting of adjacent stent segments during the dog-boning phenomenon. The interlocking joint design may maintain axial and circumferential engagement to inhibit the stent segments from losing their relative orientation to one another during delivery and partial expansion events like dog-boning. When the stent is implanted in a body vessel, the stent architecture of the now discrete axial stent segments separated from one another at deployment may provide at least one of the following: more uniform radial expansion; suitably high radial force and high circumferential compression resistance to hold lesion out of vessel lumen; suitable longitudinal flexibility and conformability for tortuous vessels; and greater bending and longitudinal compression from vessel contributing high-level motion environments. In addition, the mating elements forming the interlocking may be micro-mating elements or may be as small as possible (such as less than the strut width) to minimize body tissue interaction, yet perform at least one of the functions as detailed above.

In the present application, the term "introduction end" when referring to a delivery device refers to a direction that is farthest away from an operator using a delivery device, and intended to be inserted within a patient during a procedure. The term "operator end" refers to a direction that is generally closest to the operator using the delivery device, and generally remains outside a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits).

Figure 4:
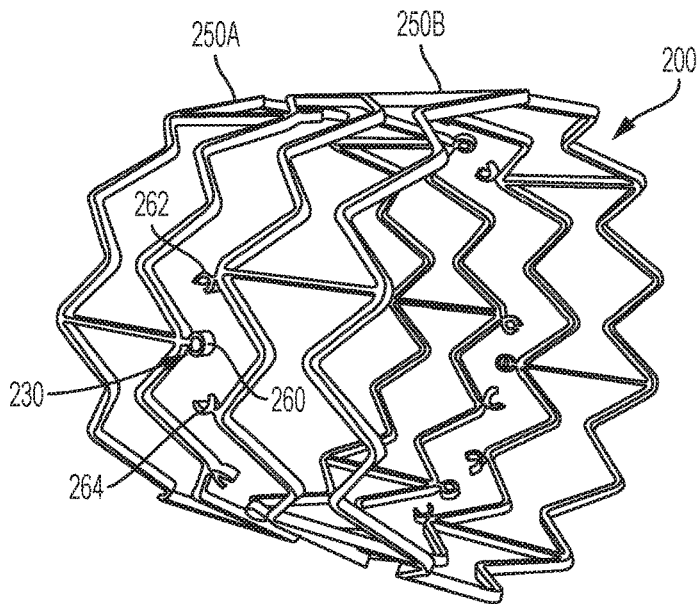
FIG. 4 is a perspective view of the stent illustrated in FIG. 1 in a radially compressed configuration.

FIG. 1 shows an example of a stent 200 in an unexpanded or radially compressed configuration. The stent 200 may be in the radially compressed configuration when loaded onto a balloon deployment system and constrained by an outer sheath, and eventually delivered to a target site at the point of treatment within a body vessel of a patient. FIG. 4 shows the stent 200 in a radially expanded configuration. The stent 200 may be movable in the radially expanded configuration when unloaded from the deployment system by retraction and removal of the outer sheath from the stent 200 and/or expansion of a balloon, thereby allowing the stent 200 to expand to a relatively larger diameter and exert an outward force on an interior wall of the body vessel. Once expanded, the stent 200 may provide the desired support to the body vessel at the point of treatment, as well as other benefits.

The stent 200 includes a plurality of stent segments coupled together by a plurality of interlocking joints 230. Axial restrictor members 232 extend from portions of the stent segments. Axial restrictor members 232 are configured to inhibit the movement of the components of the interlocking joints from moving during radial expansion such that the adjacent stent segments after disengagement maintain axial spacing relative to one another. In one example, the axial stent segments comprise one or more ring structures 212A-D disposed axially relative to one another along a longitudinal axis 215. The stent 200 is defined as a tubular body 216 defining a lumen 220 disposed about the longitudinal axis 215 between an inflow end 222 and an outflow end 224. The tubular body 216 includes an exterior surface 225 to contact the body vessel wall and an opposite, interior surface 227 facing the lumen 220. Adjacent ring structures (for example, a first ring structure 212B and a second ring structure 212C) may be coupled to one another by the interlocking joints 230. Also shown is that adjacent ring structures (for example, the second ring structure 212C and a third ring structure 212D) may be interconnected by a plurality of connector bridges 235.

Figure 2:
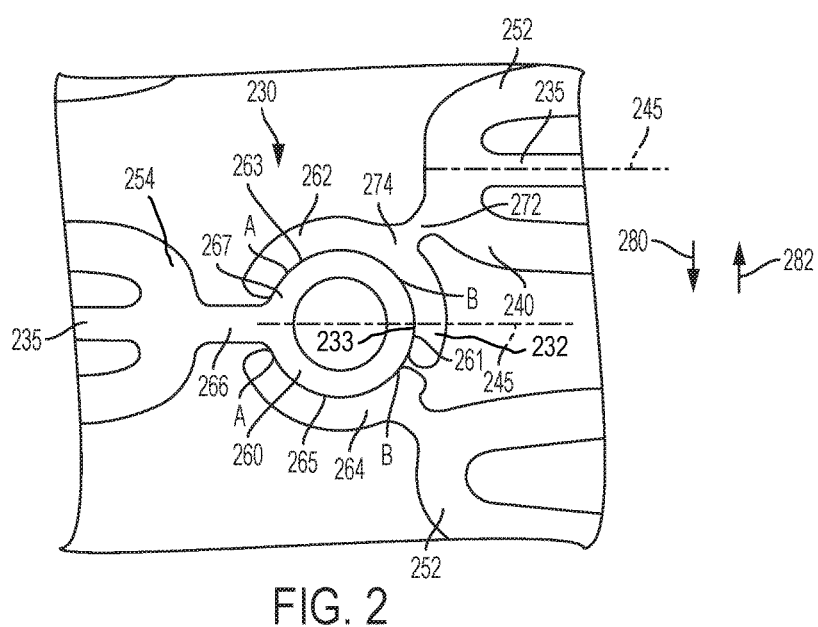
FIG. 2 is a magnified view of a plurality of mating elements forming the interlocking joint of the stent illustrated in FIG. 1.
Figure 3:
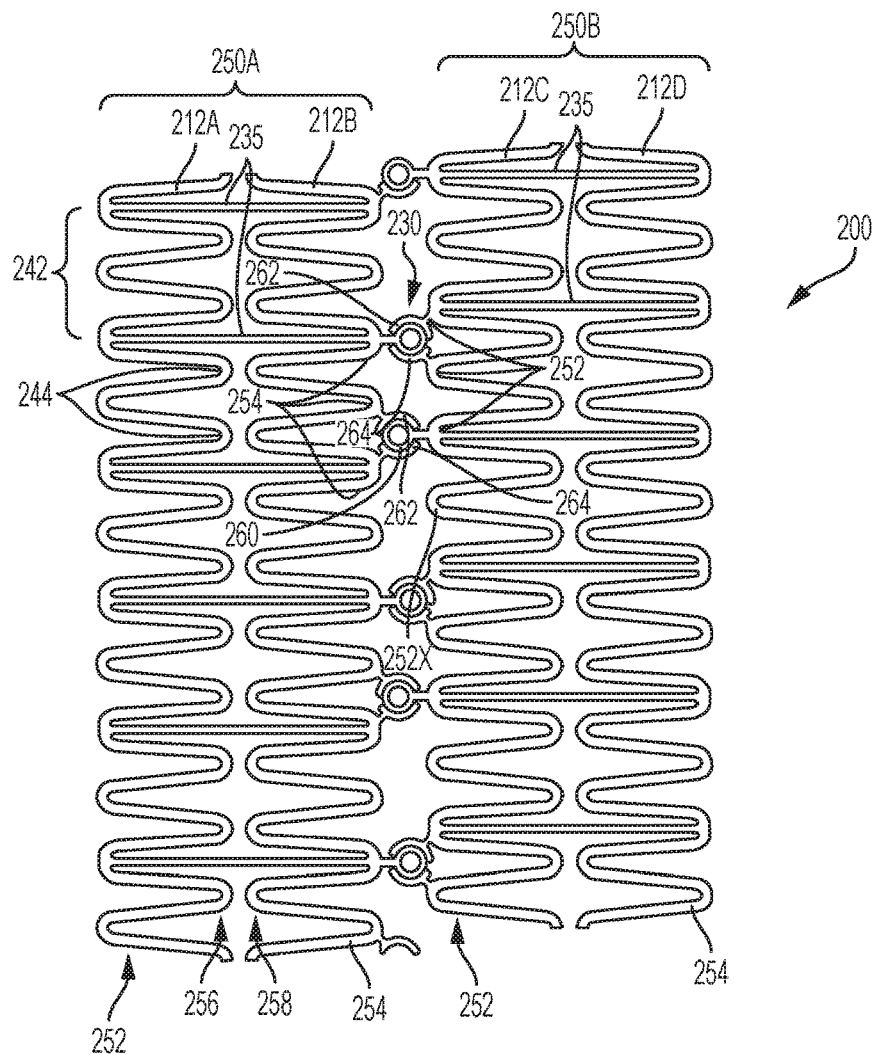
FIG. 3 is a flat pattern view of another example of a stent shown in a radially compressed configuration.

FIGS. 1-3 depict the stent 200 including a plurality of ring structure or segments (four shown as ring structures 212A, 212B, 212C, 212D). Adjacent ring structures (the second ring structure 212B and the third ring structure 212C) are shown interconnected by interlocking joints 230. Each of the ring structures 212A, 212B, 212C, 212D may have a substantially circular ring shape comprising an undulating arrangement of interconnected unit stent struts 240, such as, for example, in the serpentine or zigzag pattern shown. A pair of stent struts 240 converges toward one another and coupled to one another to define the corresponding apex at substantially the same angle relative to a principle axis 245. The principle axis 245 is shown extending through the center of an apex tip 246 and dividing the corresponding apex into apex halves. When the apex 242 is curved, a radius of curvature is defined from a center point that is disposed along the principle axis 245.

FIG. 1 shows a pair of adjacent ring structures 212A, 212B interconnected by at least one connector bridge 235 to define a first axial stent member 250A. Another pair of adjacent ring structures 212C, 212D interconnected by at least one connector bridge 235 defines a second axial stent member 250B disposed adjacent to the first axial stent member 250A.

The first series of apices 242 (or proximal apices) of the first ring structure 212A and the second series of apices 244 (or distal apices) of the second ring structure 212B define the first outer apices 252 and the second outer apices 254, respectively, of the first axial stent member 250A. The second series of apices 244 of the first ring structure 212A (or distal apices) and the first series of apices 242 of the second ring structure 212B (or proximal apices) define the first inner apices 256 and the second inner apices 258, respectively, of the first axial stent member 250A. The first inner apices 256 and the second inner apices 258 may be disposed across from another as shown in a confronting relationship and circumferentially aligned to define a peak-to-peak arrangement. In a peak-to-peak arrangement, distal apices of a first zigzag stent member and proximal apices of a second zigzag stent member (or the peaks) are circumferentially aligned with one another, and proximal apices of the first zigzag stent member and distal apices of the second zigzag stent member (or the valleys) are circumferentially aligned with one another.

The connector bridge 235 is shown coupled between a pair of the first outer apex 252 and the second outer apex 254. FIG. 3 shows the connector bridge 235 coupled between every other pair of outer apices 252, 254. In other examples, the connector bridges 235 may be disposed skipping more than one pair of outer apices 252, 254, or alternatively, may be coupled between each pair of the outer apices 252, 254. Connector bridges 235, stent struts 240 of adjacent ring structures 212, and outer apices 252, 254 may be arranged as shown to define a plurality of closed cells 259, as shown in FIG. 1. The closed cells 259 may be circumferentially spaced from one another. At least a portion of the first inner apices 256 and the second inner apices 258 may remain uncoupled to one another. In one example, all of the apices 256 and apices 258 remain uncoupled.

The outer apices 252 (or distal apices) of the first axial stent member 250A and the outer apices 254 (or proximal apices) of the second axial stent member 250B are shown in FIG. 1 and FIG. 3 disposed circumferentially offset from another to define a peak-to-valley arrangement. In a peak-to-valley arrangement, distal apices of a first zigzag stent member (or the peaks) and distal apices of a second zigzag stent member (or the valleys) are circumferentially aligned with one another, and proximal apices of the first zigzag stent member (or the valleys) and proximal apices of the second zigzag stent member (or the peaks) are circumferentially aligned with one another. The inner apices 258 of the first axial stent member 250A may be circumferentially aligned with the outer apices 254 of the second axial stent member 250B. In one example, the adjacent ring structures 212A, 212B of the first axial stent member 250A are in a peak-to-peak arrangement, the adjacent ring structures 212C, 212D of the second axial stent member 250B are in a peak-to-peak arrangement. The first axial stent member 250A and the second axial stent member 250B are in a peak-to-valley arrangement. To this end, the second ring structure 212B and the third ring structure 212C that are interconnected by interlocking joints 230 are in the peak-to-valley arrangement.

FIG. 2 depicts in further detail an example of the interlocking joint 230. The interlocking joint 230 is comprised of a mating element 260 (referred to as the first mating element) and a pair of opposite facing mating elements 262, 264 (referred to as the second and third mating elements or the first and second mating arms). The mating element 260 includes a mating surface 261 that is removably engageable with mating surfaces 263, 265 of the respective mating elements 262, 264. In one example, the mating surface 261 is complementarily shaped for the shape of the mating surfaces 263, 265. The interlocking joint 230 may be coupled between outer apices of adjacent ring structures 212A-D and/or axial stent members 250A-B. For example, the interlocking joint 230 is shown to comprise of the mating element 260 extending from one of the first outer apices 254 of the first axial stent member 250A and the mating elements 262, 264 extending from a pair of adjacent second outer apices 252 of the second axial stent member 250B. In one example, the mating element 260 may extend from the same axial stent member, such as, the first axial stent member 250A, and the other mating elements 262, 264 extend from the other axial stent member. In another example, the mating elements 260 may alternate between the first and second axial stent members, and the other mating elements 262, 264 correspondingly alternate between the other of the first and second axial stent members.

FIG. 2 shows the mating element 260 projecting from the outer apex 254. The mating element 260 includes a base stem 266 extending from or coupled to the respective outer apex 254 and an enlarged mating tip 267 extending from the base stem 266 about the principle axis 245. The enlarged mating tip 267 has a larger surface area than the base stem 266. The shape of the enlarged mating tip 267 is shown having a ring shape. In other examples, the enlarged mating tip 267 may include other shapes, such as, but not limited to, circular, elliptical, ovalic, and rectangular. The mating surface 261 is defined by the perimeter surface of the enlarged mating tip 267, and is shown extending in both circumferential directions 280, 282. In the example shown, the mating surface 261 includes a circular or convex portion facing along the first circumferential direction 280 to engage with the mating surface 265 of the mating element 264 and a circular or convex portion facing along the second circumferential direction 282 to engage with the mating surface 263 of the mating element 262. Other shapes, such as rectangular, would provide the mating surface 261 with more planar surface, as appreciated by one of ordinary skill in the art. In one example, the mating element 260 is shown extending from the outer apex 254 that is associated with the connector bridge 235. Alternatively, the mating element 260 may extend from the outer apex where the connector bridge is omitted.

The mating elements 262, 264 may be mirror images of one another and face in different circumferential directions. Accordingly, the following description will now focus on the mating element 262, and it can be appreciated by one of ordinary skill in art to associate the description with the other mating element 264. The mating elements 262 includes the base stem 272 coupled to the respective outer apices (shown as apex 252) and the mating tip 274 extending from the corresponding base stem 272. In one example, the base stem 272 is coupled to the apex half portion of the apex 252. The mating tip 274 may be extended circumferentially from the base stem 272 in the circumferential direction away from the respective principle axis 245 of the apex 252.

The mating surface 263 of the mating element 262 may be defined by the circumferentially facing surface of the mating tip 274. The mating surface 263 is complementarily shaped to couple with the shape of the mating surface 261 of the mating element 260. For example, when the shape of the enlarged mating tip 267 is circular, the mating surface 263 includes a circular or concave portion facing along the first circumferential direction 280 to engage with the respective convex portion of the mating surface 261 of the mating element 264. In this example, the mating tip 274 may be described as having a C-shape. To this end, the concave portion of the mating surface 263 may be defined by a radius of curvature that is larger than the circular convex portion of the mating surface 261. The mating surface 265 would similarly include a circular or concave portion facing along the second circumferential direction 282 to engage with a different convex portion of the mating surface 261 of the mating element 264. The radius of curvature of the mating surface 265 that is larger than the corresponding circular convex portion of the mating surface 261. In one example, the mating element 262 extends from the outer apex 252 that is associated with the connector bridge 235, the mating element 264 is shown extending from the respective outer apex 252 that is not coupled to the connector bridge 235.

When in the interlocking relationship, the first mating element 260 is received within the second and third mating elements 262, 264. When received, the first mating element 260 is captured or sandwiched between the mating surfaces 263, 265 of the respective mating elements 260, 262 to define the interlocking joint 230. The mating elements 262, 264 engage the mating element 260 at a points or surfaces of engagement A, B for maintaining axial engagement along both axial directions to inhibit relative axial displacement between each other and resist axial elongation or shortening of the stent 200 under respective tensile and compression loads when the stent is in the radially compressed configuration. The engagement between the mating surface 261 of the mating tip 274 and the mating surfaces 263, 265 of the mating elements 262, 263 may further inhibit circumferential displacement away from each other in the circumferential directions 280, 282 under torque loading. The circumferential engagement and the axial engagement between the mating elements 260, 262, 264 may be along the plane P that is obliquely extended relative to the principle axis 245.

FIG. 3 illustrates one pattern for the stent 200. Here, three consecutive outer apices, for example, the outer apices 252 of the second axial stent member 250B, include the mating element 262, the mating element 264, and the mating element 260 in sequential order. An outer apex without a mating element, shown as the outer apex 252X, may be interposed between the pattern of mating elements. Three consecutive outer apices, for example, the outer apices 254 of the first axial stent member 250A, include the mating element 260, the mating element 262, and the mating element 264 is also in sequential order to complement the pattern of mating elements found in the second axial stent member 250B. The stent 200 may include alternating arrangements of interlocking joints 230. The alternating arrangement may include the mating element 260 extending from the outer apex 254 of one of the axial stent members, for example, axial stent member 250A, and the mating elements 262, 264 extend from the outer apex 252 from the other axial stent member, for example, axial stent member 250B, at one interlocking joint. The adjacent interlocking joint includes the mating element 260 extending from the outer apex 252 of the other axial stent member 250B and the mating elements 262, 264 extending from the outer apex 254 of the one of the axial stent member 250A.

The interlocking joints 230 couple adjacent stent segments, such as, for example, axial stent members 250A, 250B and/or ring structures 212A-D, when the stent 200 is in the radially compressed configuration. This coupling may maintain the relative position of the axial stent members and/or ring structures during delivery of the stent to its target site. Once radial expansion initiates, the interlocking joints 230 are configured to disengage or uncouple. Once disengaged from one another, the axial stent members and/or ring structures function as a plurality of discrete stent members may be axially spaced from one another by a longitudinal distance, as will be described, when implanted into the body vessel at the target site with a single deployment system. In some instances, the interlocking joints 230 may disengage prior to full radial expansion of the stent 200, such as, for example, but not limited to, at 25% of the diameter at full expansion. The interlocking joints 230 may disengage at approximately the same expansion diameter. Alternatively, a portion of the interlocking joints 230 may disengage at different expansion diameters depending on the location and configuration of the interlocking joints 230 along the curvature of the body vessel and the configuration and expansion of the balloon deployment system. After expansion, the unlocking and distance between the discrete axial stent members permit relative axial displacement between the stent members as a body vessels changes in configuration.

FIG. 4 shows the stent 200 in the radially expanded configuration. The mating elements 262, 264 are circumferentially moved relative to the mating element 260. Here, the mating element 264, associated with the outer apex without the connector bridge, may also move axially relative to the mating elements 260, 262. As a result, the axial stent members 250A, 250B become independent, discrete support structures implanted within the respective body vessel. The axial stent members 250A, 250B are axially spaced from another by the longitudinal distance to permit relative axial movement or displacement between the axial stent segments and better withstand loading from the body vessel is in a high motion environment.

To inhibit the movement of the first mating element 260 of the interlocking joint 230 in the first longitudinal direction during radial expansion such that the first and second stent segments (for example, the first and second axial stent members 250A, 250B) maintain axial spacing relative to one another after disengagement, the axial restrictor members 232 may be provided. FIGS. 5-8 show various examples of the axial restrictor members 232. Although the engaging axial surface of any of the axial restrictor members described herein are shown having a shape that complements the shape of the mating element for engagement fit. In one example, the engaging axial surface of the axial restrictor members are shown to have a concave shape that complements the rounded shape of the mating element. In alternative examples, the axial restrictor members may have other shapes that may not complement the shape of the mating element.

FIG. 5 shows a first example of the axial restrictor member 232 configured as a circumferential extension of a mating tip of one of the second or third mating elements (shown extending from the mating tip 274 of the second mating element 262). This axial restrictor member 232 extends circumferentially to an axial location relative to the first mating element and proximate the principal axis 245 (crossing the axis (as shown) or terminating short of the axis). In this example, the engaging axial facing surface 233 of the axial restrictor member 232 is continuous with the mating surface 263 of the second mating element 262. In one example, the second mating element 262 and the axial restrictor member 232 together may form a continuous C-shaped element 300 extending circumferentially about 150 degrees to 190 degrees (shown as 180 degrees) around the first mating element 260. The other third mating element 264 may form a C-shaped element extending circumferentially less than the second mating element 262 (shown extending about 60 degrees to 120 degrees around the first mating element 260). In another example, the axial restrictor member 232 may circumferentially extend from the base stem 272 of the mating element 262, rather than the mating tip 274, to the axial location proximate the principal axis. In another example, the axial restrictor member 232 may circumferentially extend from the outer apex 245 in close proximity to the landing of the base stem 272 to the axial location proximate the principal axis. The side edges that define the base stem 272 may be separated from one another by a distance less than the distance between the outer apex 254 and the mating tip 274 of the second mating element 262 from a location farther away from the outer apex 254.

The axial restrictor member may further include a reinforcement support member that is configured to provide additional strength to the axial restrictor member to withstand axial loading from the first mating element 260 during expansion. The reinforcement support element may be coupled to the axial restrictor member and the first mating element to provide additional strength to the base stem 272 for withstanding a moment load from the first mating element 260 during expansion.

FIG. 6 shows the axial restrictor member (now referred to as axial restrictor member 315) with a reinforcement support member 310. The axial restrictor member 315 and the reinforcement member 310 may be formed integrally as a single restrictor unit 318, as shown, shown having a relatively thickened base stem. In this example, the single restrictor unit 318 includes an engaging axial surface 320 facing the mating element 260, a first edge 322 extending between the mating tip and the outer apex 254, and a second edge 324. The second edge 324 is disposed circumferentially opposite to the first edge 322 and extends between the mating tip 274 of the second mating element 262 and a location along the strut 240 farther away from the outer apex 254 than the first edge 272. The second edge 324 may be separated from the first edge 322 by at least the distance of the stem element defined between the outer apex 254 and the mating tip 274 of the second mating element 262 from a location farther away from the outer apex 254.

FIG. 7 shows an alternative single restrictor unit (now referred to as 330) defining the reinforcement support member. The single restrictor unit 330 includes the engaging axial surface 332 facing the mating element 260, the first edge 334 extending between the mating tip and the outer apex 254, and the second edge 336. The second edge 336 is disposed circumferentially opposite to the first edge 334. The second edge 336 extends between the reinforcement support member portion 337 of the single restrictor unit 330 and any one location between an intermediate of the strut 240 and the inner apex 258. The restrictor unit 330 includes a greater mass than the unit 318 and thus has greater material for support. Any one of the restrictor units 318 or 330 may be solid, as shown, or may comprise of interconnected struts suitably positioned for enhanced support. The restrictor unit 318 or 330 may be attached to the strut of the axial stent member in a separate process or may be formed integrally with the strut, such as, for example, during a laser cutting operation.

FIG. 8 shows the axial restrictor member (now referred to as axial restrictor member 340) with the reinforcement support member 342. The axial restrictor member 340 and the reinforcement member 342 may be coupled to one another or formed integrally together to form a single restrictor unit 345, as shown. In this example, the axial restrictor member 340 includes an engaging axial surface 350 facing the mating element 260. The reinforcement support member 342 includes a longitudinal strut body 352 extending from any location from proximate the inner apex 258 to an intermediate of the strut 240. The strut body 352 may be disposed about the principal axis 245. The strut body 352 coupled to an intermediate location along the side 354 of the axial restrictor member 340 opposite the engaging axial surface 350. The axial restrictor member 340 is shown extending circumferentially away from the principal axis 245 toward one or both of the second and third mating elements 262, 264.

Figure 9:
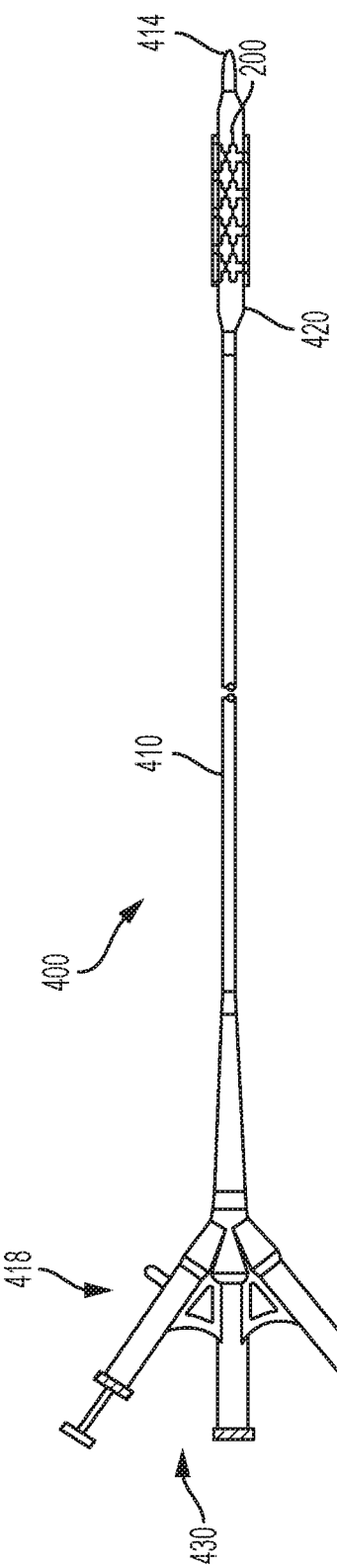
FIG. 9 is a side view of a delivery device for an example of a stent.

FIG. 9 is a schematic of a delivery system 400 for the stent 200 with the mating element configurations with any of the disclosed axial restrictor members. The stent 200 is designed to be percutaneously delivered through a body lumen of a body vessel to a target site. The target site may be, for example, a location in the artery system of a patient, such as, for example, the superficial femoral artery (SFA). The delivery system 400 includes a catheter 410 having a proximal, introduction end 414 and a distal, operator end 418. A balloon 420 is positioned on the introduction end 414 of the catheter 410. A connector assembly 430 is disposed at the operator end 418 of the catheter 410 and is adapted to facilitate expansion of the balloon 420 as is known in the art. The connector assembly 430 provides access to one or more interior lumens of the catheter 410 to provide access to the interior of the balloon 420, and possibly a guidewire (not illustrated) or other conventional components or for the introduction of bioagents or other medicinal fluids. The stent 200 is disposed at the introduction end 414 of the catheter 410. For example, the stent 200 surrounds the deflated balloon 420 (typically crimped on the balloon) and is initially, prior to placement in a body vessel, in its radially compressed configuration. The stent 200 may be further maintained in the radially compressed configuration prior to deployment of the stent 10 to its radially expanded configuration by any suitable means, including a sheath, a suture, a trigger wire, a tube or other restraining material around all or part of the compressed stent, or other methods. The exterior surface of the balloon 420, upon inflation, will radially expand and contact to apply radial pressure along the interior surface of the stent 200, moving the stent 200 to its radially expanded configuration.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments. An appropriately sized delivery catheter can be selected by one skilled in the art for a given application. For example, some examples can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some examples, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheter.

As indicated above, and with additional reference to FIG. 10, the present disclosure is well-suited for providing artificial support to a body vessel 500 in need of such support. This can be performed by inserting the introduction end 414 of the catheter 410 into the lumen of the body vessel 500 and navigating the introduction end 414, and the loaded stent 200, to a point of treatment or target site 510 in the vessel 500 in need of radial support. The catheter 410 can be placed over a guidewire (not illustrated) to facilitate navigation.

The mating elements that form the interlocking joints of the stent 200 are maintained in the interlocking relationship. During tracking, maneuvering, and orienting the stent to the point of treatment, the stent 200 having the interlocking joint(s) 230 are configured to suitably flex, bend longitudinally, and/or withstand plastic deformation due to axial and/or torque loading that would be commonly associated with balloon expandable stents. The interlocking joint design may maintain axial and circumferential engagement and inhibit the stent segments from losing their relative orientation to one another during tracking, maneuvering, and orienting and during dog-boning from balloon expansion. The dog-boning phenomenon D is shown in FIG. 10. The dog-boning phenomenon is a result of inward axially compressive forces induced from the stent's resistance to expand and the obliquely oriented balloon expansion force during balloon expansion. The inward force causes the stent segments to push against the adjacent stent segments, resulting in overlapping and stent buckling. The dog-boning phenomenon may cause axial displacement of the mating elements, also known as microsliding, (and thus the stent segments) toward one another and result in stent segment overlapping during deployment.

FIGS. 11A-11D depict sequential events during radial expansion of the stent 200 from the radially compressed configuration (FIG. 11A) to the radially expanded configuration (FIG. 11D). According to FIG. 11B, the axial restrictor member 232 is positioned to inhibit or block the mating element 260 (and thus the second axial stent member 250B) from such axial displacement in the direction of the arrow 600 during the dog-boning phenomenon. The axial restrictor member 232 is positioned to inhibit or block the mating element 262 (and thus the first axial stent member 250A) from axial displacement in the direction opposite the direction of the arrow 600 during the dog-boning phenomenon. As the interlocking joint 230 unlocks, the axial restrictor member 232 may resist the inward force push to overcome the urge for overlapping and unnatural stent buckling that leads to uneven spacing of the stent segment deployment. During continued expansion, the mating elements 262, 264 circumferentially move away from the mating element 260 (as shown by arrows 602, 604, respectively, in FIG. 11C) and expansion of the stent 200 is to a point where the induced inward force from dog-boning that causes axial movement is minimal. To this end, the mating element configuration of the interlocking joints with the axial restrictor members may increase mechanical stability of the mating element and provide more evenly spaced deployment of the segmented stent in situ.

Once the stent 10 is disposed at the point of treatment, the balloon 420 may be inflated in the conventional manner. Inflation of the balloon 420 forces the stent 200 to radially expand. During radial expansion, in which the stent 200 changes from the radially compressed configuration to its radially expanded configuration, the interlocking joints 230 disengage from their interlocking relationship. The interlocking relationship may be broken when the expansion reaches a certain percentage of full expansion diameter, for example, about 25%. The percentage could be greater or lesser depending on the balance of a desirable orientation of the stent segments at implantation and a desirable separation length between the segments at implantation. A larger percentage may aid in a more desirable orientation but allow for less separation, and vice versa. Following expansion, the balloon 420 may be deflated, leaving the stent 200 in its radially expanded configuration. The catheter 410 may then be withdrawn from the vessel 500, leaving the stent 200 in its radially expanded configuration at the point of treatment 510 within the body vessel as shown in FIG. 10. The stent 10 is now configured as a series of discrete ring structures and/or axial stent members axially spaced from another.

The stents described herein may be configured to survive high motion environment loads, such as, for example, the SFA, without experiencing permanent deformation and provide higher radial force and greater compression resistance than that found with self-expanding stents. The effect may include to have a series of discrete stent segments deployed in the vessel with a small region of unstented vessel between segments. When the vessel moves, for example bending, the unstented regions of the vessel are able to move and accommodate the bending load without affecting the stented regions, thereby preventing permanent deformation of the stent. The interlocking joints included with the stents hold the segments together, for example, while on the balloon catheter, and the subsequent separation of the segments after, for example, balloon expansion, to maximize flexibility of the stented vessel.

The shape, size, and dimensions of the stent segments, for example, each of the ring structures and/or axial stent members, of the stent may vary. The size of these components and the overall stent is determined primarily by the diameter of the vessel lumen at the intended implant site, as well as the desired length of the overall stent device. The ring structures and/or axial stent members may have a common cross-sectional area. Alternatively, a first ring structure and/or stent segment may have a first cross-sectional area, a second ring structure and/or stent segment may have a second, larger cross-sectional area.

The term "stent" means any device or structure that provides or is configured to provide rigidity, expansion force, or support to a body part, for example, a diseased, damaged, or otherwise compromised body lumen. The stent may include any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane. The stent may be "expandable," that is, it may be capable of being expanded to a larger-dimension configuration. The stent may expand by virtue of its own resilience (i.e., self-expanding), upon the application of an external force (i.e., balloon-expandable), or by a combination of both. In one example, the stent may have one or more self-expanding portions and one or more balloon-expandable portions. The stent struts that are interconnected to one another represents specific configurations of a wire member that comprises a basic structural component of the stent. As used herein, the term "strut" refers to any filamentary member, including, but not limited to, drawn wire and filaments that have been laser cut from a cannula. For example, the stent architecture with the intricate mating elements that form the interlocking joints may lend itself to being manufacture from a metal cannula laser cut to the desired pattern as described. The stent architecture of the stent 200 may include any one or a combination of any of the configuration of the interlocking joints 230 to define even more different configurations of stents. The design of the interlocking joints may allow for standard manufacturing processes and handling/crimping of the stent and avoid complex manufacturing or special care.

The stent 200 may be associated with a graft to form a stent graft. For example, the stents may be coupled along an interior, exterior, or both surface of the graft tubular body by suture attachments. The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biological material. Examples of suitable synthetic materials include fabrics, woven and non-woven materials, and porous and non-porous sheet materials. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS. In one example, low profile graft material is provided, which can be about one-half the thickness of the stent member.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent disposed about a longitudinal axis, the stent having a radially compressed configuration and a radially expanded configuration, the stent comprising:
   a first stent segment disposed about the longitudinal axis and a plurality of stent struts forming a plurality of first outer apices that extend in a first longitudinal direction;
   a second stent segment disposed about the longitudinal axis and axially adjacent to the first stent segment, the second stent segment having a plurality of stent struts forming a plurality of second outer apices that extend in a second longitudinal direction, opposite the first longitudinal direction; and
   a plurality of interlocking joints removably coupling the first stent segment and the second stent segment together, each of the interlocking joints comprising a first mating element, a second mating element, and a third mating element, wherein the first mating element extends away from one of the first outer apices, the second mating element and the third mating element extend away from adjacent outer apices of the second outer apices, and an axial restrictor member extending away from the second stent segment, wherein, in the radially compressed configuration, the second and third mating elements are circumferentially engageable with the first mating element, and the axial restrictor member is axially engageable with the first mating element, and
   wherein, in the radially compressed configuration, the axial restrictor member extends from one of the second and third mating elements and crosses a principle axis of one of the interlocking joints, while the other one of the second and third mating elements does not cross the principle axis, where the principle axis extends in a longitudinal direction of the stent and passes through a center of the first outer apex of the interlocking joint.

2. The stent of claim 1, wherein the axial restrictor member comprises an engaging axial surface facing the first mating element.

3. The stent of claim 2, wherein the engaging axial surface is concave.

4. The stent of claim 1, wherein the axial restrictor member is coupled to one of the second and third mating elements.

5. The stent of claim 4, wherein the axial restrictor member is a circumferential extension of one of the second and third mating elements.

6. The stent of claim 5, wherein the second mating element and the axial restrictor member together form a C-shaped element.

7. The stent of claim 6, wherein the third mating element has a smaller circumferential extension than the C-shaped element.

8. The stent of claim 1, wherein, during radial expansion to the radially expanded configuration, the first mating element disengages from the second and third mating elements, and the axial restrictor member is configured to inhibit the movement of the first mating element in the first longitudinal direction such that the first and second stent segments after disengagement maintain axial spacing relative to one another.

9. The stent of claim 1, wherein the axial restrictor member includes a reinforcement support element.

10. The stent of claim 9, wherein the axial restrictor member is coupled to the second mating element, and the reinforcement support element is coupled between the axial restrictor member and the second mating element.

11. The stent of claim 9, wherein the reinforcement support element comprises a longitudinal strut coupled between the axial restrictor member and the second stent segment.

12. A stent disposed about a longitudinal axis, the stent having a radially compressed configuration and a radially expanded configuration, the stent comprising:
   a first stent segment disposed about the longitudinal axis, the first stent segment including a plurality of first outer apices extending in a first longitudinal direction, and a first rounded mating head extending in the first longitudinal direction from at least one of the first outer apices; and
   a second stent segment disposed about the longitudinal axis and axially adjacent to the first stent segment, the second stent segment including a plurality of second outer apices extending in a second longitudinal direction, and a first concave mating arm and a second concave mating arm, where the first mating arm extends from a first outer apex of the second outer apices and the second mating arm extends from a second outer apex of the second outer apices, and an axial restrictor member extending from the second stent segment,
   wherein, in the radially compressed configuration, the first concave mating arm and the second concave mating arm are engageable along different circumferential sides of the first rounded mating head.

13. The stent of claim 12, wherein the axial restrictor member comprises an engaging axial concave surface facing the first rounded mating head.

14. The stent of claim 13, wherein the axial restrictor member is a circumferential extension of one of the first and second concave mating arms.

15. The stent of claim 13, wherein the axial restrictor member includes a reinforcement support element.

16. The stent of claim 15, wherein the axial restrictor member is coupled to the first concave mating arm, and the reinforcement support element is coupled to the axial restrictor member and the first concave mating arm.

17. The stent of claim 12, wherein, during radial expansion to the radially expanded configuration, the first rounded mating head disengages from the first and second concave mating arms, and the axial restrictor member is axially engageable with the first rounded mating head to inhibit relative axial movement of the first and second stent segments closer to one another such that the first and second stent segments after disengagement maintain axial spacing relative to one another.

18. A stent disposed about a longitudinal axis, the stent having a radially compressed configuration and a radially expanded configuration, the stent comprising:
   a first stent segment and a second stent segment adjacent thereto and disposed about the longitudinal axis, the first stent segment including a plurality of first outer apices that extend in a first longitudinal direction, at least one of the first outer apices including a first mating element, the second stent segment including a plurality of second outer apices that extend in a second, opposite longitudinal direction, a pair of adjacent second outer apices including a second mating element and a third mating element, respectively, wherein the second stent segment includes an axial restrictor member having an engaging axial surface contactable with the first mating element during radial expansion,
   wherein, in the radially compressed configuration, the first mating element is circumferentially captured between the second and third mating elements,
   wherein the second mating element extends away from a first outer apex of the second outer apices and the third mating element extends away from a second outer apex of the second outer apices.

19. The stent of claim 18, wherein the engaging axial facing surface is continuous with a mating surface defined by the second mating element.

20. The stent of claim 18, wherein, during radial expansion to the radially expanded configuration, the first rounded mating head disengages from the first and second concave mating arms, and the axial restrictor member is axially engageable with the first rounded mating head to inhibit relative axial movement of the first and second stent segments closer to one another such that the first and second stent segments after disengagement maintain axial spacing relative to one another.

* * * * *